(12) United States Patent
Khan et al.

(10) Patent No.: US 12,282,018 B2
(45) Date of Patent: Apr. 22, 2025

(54) SYSTEM AND METHOD FOR TRANSISTOR PATHOGEN DETECTOR

(71) Applicant: AKHAN Semiconductor, Inc., Gurnee, IL (US)

(72) Inventors: Adam Khan, San Francisco, CA (US); Ernest Schirmann, Lake Zurich, IL (US); Kiran Kumar Kovi, Lisle, IL (US)

(73) Assignee: AKHAN SEMICONDUCTOR, INC., Gurnee, IL (US)

( * ) Notice: Subject to any disclaimer, the term of this patent is extended or adjusted under 35 U.S.C. 154(b) by 0 days.

(21) Appl. No.: 18/734,733

(22) Filed: Jun. 5, 2024

(65) Prior Publication Data
US 2024/0345089 A1 Oct. 17, 2024

Related U.S. Application Data

(63) Continuation of application No. 17/234,709, filed on Apr. 19, 2021, now Pat. No. 12,031,987.

(60) Provisional application No. 63/011,712, filed on Apr. 17, 2020.

(51) Int. Cl.
| | | |
|---|---|---|
| B32B 9/00 | (2006.01) |
| C01B 32/198 | (2017.01) |
| C01B 32/26 | (2017.01) |
| C23C 16/02 | (2006.01) |
| C23C 16/27 | (2006.01) |
| C23C 16/513 | (2006.01) |
| G01N 27/414 | (2006.01) |
| G01N 33/551 | (2006.01) |
| G01N 33/569 | (2006.01) |
| H01L 29/66 | (2006.01) |
| B82Y 5/00 | (2011.01) |
| B82Y 30/00 | (2011.01) |
| B82Y 35/00 | (2011.01) |
| B82Y 40/00 | (2011.01) |

(52) U.S. Cl.
CPC ..... *G01N 33/56983* (2013.01); *C01B 32/198* (2017.08); *C01B 32/26* (2017.08); *C23C 16/0236* (2013.01); *C23C 16/271* (2013.01); *C23C 16/274* (2013.01); *C23C 16/279* (2013.01); *C23C 16/513* (2013.01); *G01N 27/4145* (2013.01); *G01N 33/551* (2013.01); *H01L 29/66969* (2013.01); *B82Y 5/00* (2013.01); *B82Y 30/00* (2013.01); *B82Y 35/00* (2013.01); *B82Y 40/00* (2013.01); *C01B 2204/22* (2013.01); *C01B 2204/32* (2013.01); *C01P 2002/60* (2013.01); *C01P 2004/16* (2013.01); *C01P 2004/64* (2013.01); *G01N 2333/165* (2013.01)

(58) Field of Classification Search
CPC ..... Y10T 428/30; C01B 32/198; C01B 32/26; B82Y 5/00; B82Y 30/00
See application file for complete search history.

*Primary Examiner* — Daniel H Miller
(74) *Attorney, Agent, or Firm* — David R. Stevens; Stevens Law Group

(57) ABSTRACT

Disclosed herein is a system and method for transistor pathogen virus detector in which one embodiment may include a substrate layer, a silicon dioxide layer on the substrate layer, a nanocrystalline diamond layer on the silicon dioxide layer, a graphene oxide layer on the nanocrystalline diamond layer, fluorinated graphene oxide portions; and a linker layer, the linker layer including a plurality of pathogen receptors.

1 Claim, 5 Drawing Sheets

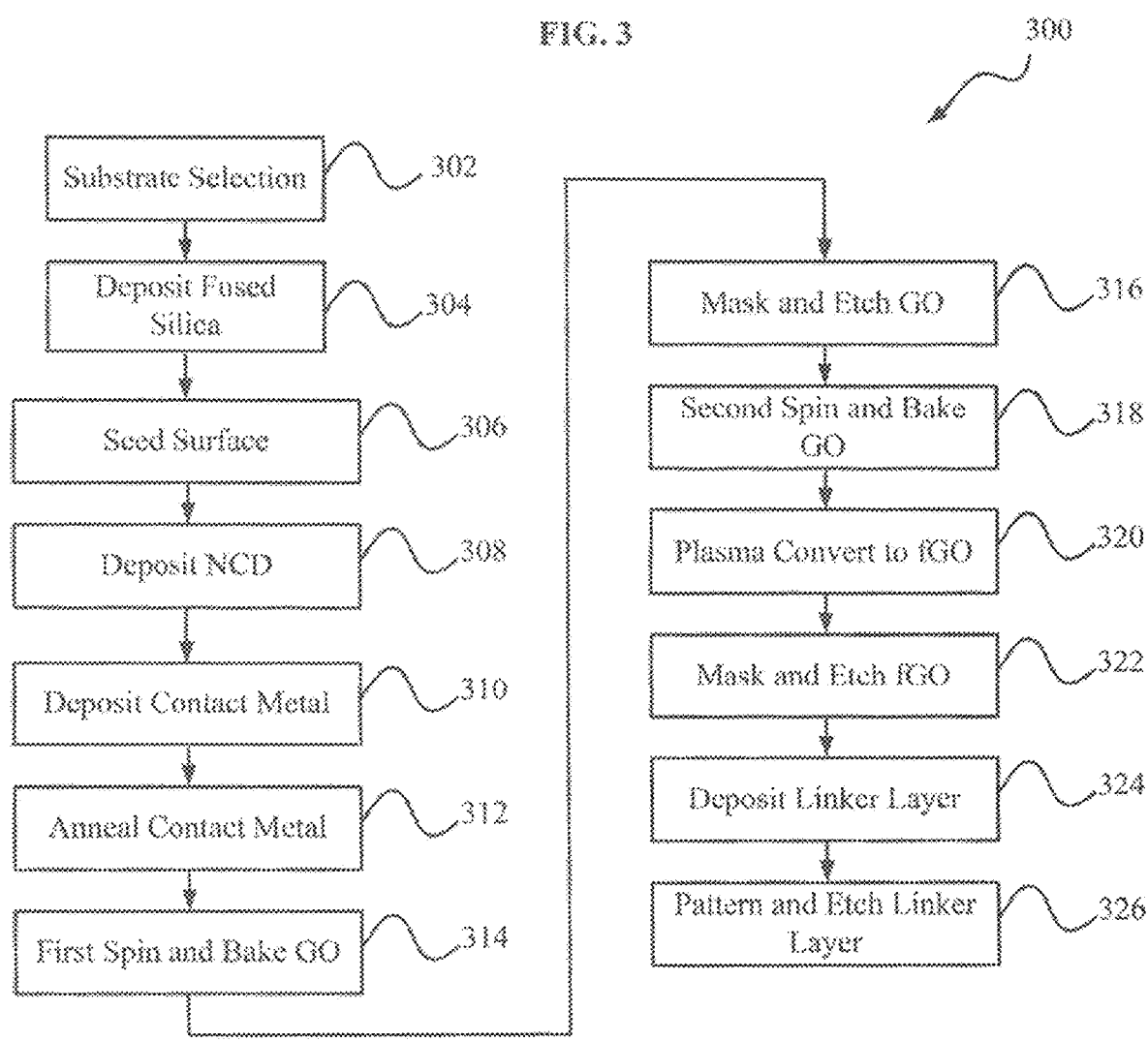

SYSTEM AND METHOD FOR TRANSISTOR PATHOGEN DETECTOR

CROSS-REFERENCE TO RELATED APPLICATIONS

This application is a continuation of U.S. patent application Ser. No. 17/234,709, filed Apr. 19, 2021, which claims the benefit of U.S. Provisional Application No. 63/011,712, filed Apr. 17, 2020, both of which are fully incorporated herein by reference.

FIELD

This invention is generally related to systems and methods for pathogen virus detection, such as the corona virus, and more particularly to a system and method for providing a diamond transistor pathogen virus detector.

BACKGROUND

The SARS-COV2 virus transmits a highly contagious, potentially fatal, human disease, COVID-19. Rapid, accurate, and early diagnosis of the SARS-COV2 virus is critical to public health containment efforts worldwide. Diamond possesses favorable theoretical semiconductor performance characteristics. The systems and methods provided herein provide a practical and efficient pathogen virus detector.

SUMMARY

Disclosed herein is a new and improved system and method for a diamond transistor pathogen virus detector. In accordance with one aspect of the approach, a transistor pathogen virus detector may include a substrate layer, a silicon dioxide layer on the substrate layer, a nanocrystalline diamond layer on the silicon dioxide layer, a graphene oxide layer on the nanocrystalline diamond layer, fluorinated graphene oxide portions; and a linker layer, the linker layer including a plurality of pathogen receptors.

In another approach, a method of fabricating a diamond transistor pathogen virus detector may include the steps of selecting a substrate; forming a silicon dioxide layer upon the substrate; forming a nanocrystalline diamond layer on the silicon dioxide layer, forming a graphene oxide layer on the nanocrystalline diamond layer, converting at least a portion of the graphene oxide layer to fluorinated graphene oxide; and forming a linker layer on at least a portion of the fluorinated graphene oxide (FGO) layer; and binding a pathogen receptor to the linker layer.

Other systems, methods, aspects, features, embodiments and advantages of the system and method disclosed herein will be, or will become, apparent to one having ordinary skill in the art upon examination of the following drawings and detailed description. It is intended that all such additional systems, methods, aspects, features, embodiments and advantages be included within this description, and be within the scope of the accompanying claims.

BRIEF DESCRIPTION OF THE DRAWINGS

It is to be understood that the drawings are solely for purpose of illustration. Furthermore, the components in the figures are not necessarily to scale, emphasis instead being placed upon illustrating the principles of the system disclosed herein. In the figures, like reference numerals designate corresponding parts throughout the different views.

FIG. 3 is an exemplary block diagram of an embodiment of a method for fabricating a diamond transistor pathogen virus detector, such as the pathogen virus detector of FIG. 1.

DETAILED DESCRIPTION

The following detailed description, which references to and incorporates the drawings, describes and illustrates one or more specific embodiments. These embodiments, offered not to limit but only to exemplify and teach, are shown and described in sufficient detail to enable those skilled in the art to practice what is claimed. Thus, for the sake of brevity, the description may omit certain information known to those of skill in the art.

Disclosed herein is a nanocrystalline diamond and reduced graphene oxide-based field-effect transistor system and method for detection of the SARS-COV2 virus and other antigen targets. This system utilizes semiconductor characteristics of carbon nanomaterials such as reduced graphene oxide, fluorinated graphene oxide, and nanocrystalline diamond. This may yield sensitive and specific detection of antigen proteins such as the S-Protein biomarker associated with SARS COV2, the N-protein biomarker associated with the SARS, and the glycoprotein associated with Ebola.

As opposed to chromatography and opto-fluidic chips, the Biosensor Field-effect transistor (Bio-FET) is an attractive platform for the rapid and accurate detection of various analytes in gases and in water. The advantages Bio-FET sensors include ultrafast response, low-cost, and ease of use, with real-time results monitored by tunable low-cost meters. A Bio-FET sensor is comprised of a semiconductor channel, which connects the source and the drain terminals. The charged biomolecule is attracted, immobilized, and then absorbed in the semiconductor which produces an electric field that changes the charge carrier density within the device. Bio-FET sensors achieve high sensitivity and selectivity for specific biomolecules by attaching specific antibody mimetic protein probes on the conducting channel, a critical factor for sensor performance. Two-dimensional (2D) semiconductor materials such as graphene and $MoS_2$ conducting channels and three-dimensional semiconductor nanowire materials such as $In_2O_3$ have been explored for Bio-FET sensors due to their superior electronic properties. Utilizing a novel combination of nanocrystalline diamond, reduced graphene oxide, and reduced fluorinated graphene oxide, Bio-FET sensors may be realized featuring both excellent channel conduction and highly insulating gate oxide materials, on biologically inert and chemically resistant thin film nanocrystalline diamond. Such a system would have control on the selective surface properties for hydrophobicity and hydrophilicity, necessary for biological use, with device ruggedness owing to the all-carbon bonding of the diamond and graphene structures.

Figure 1:
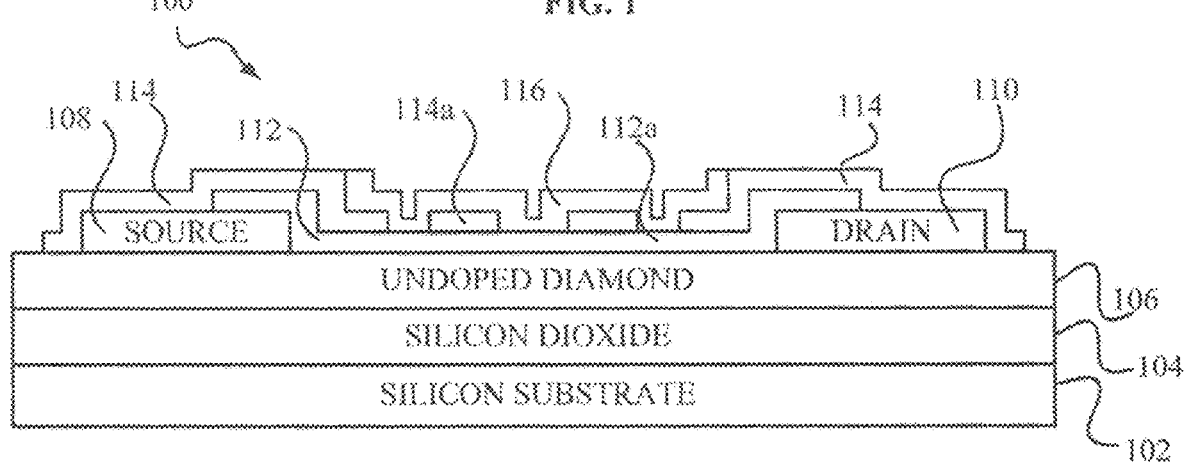
FIG. 1 is an exemplary illustrative side view of a diamond transistor pathogen virus detector.

The system and methods provided herein allow for a transistor pathogen virus detector. FIG. 1 shows an exemplary diamond transistor pathogen virus detector 100, including a silicon layer 102, a silicon dioxide layer 104, an undoped diamond layer 106, a metal layer having a source 108 portion and a drain 110 portion, a first graphene oxide (GO) layer 112, the first GO layer 112 including a GO conductive channel 112a portion, a second graphene oxide layer 114 including an FGO gate oxide 114a portion, and a linker layer 116.

Figure 2A:
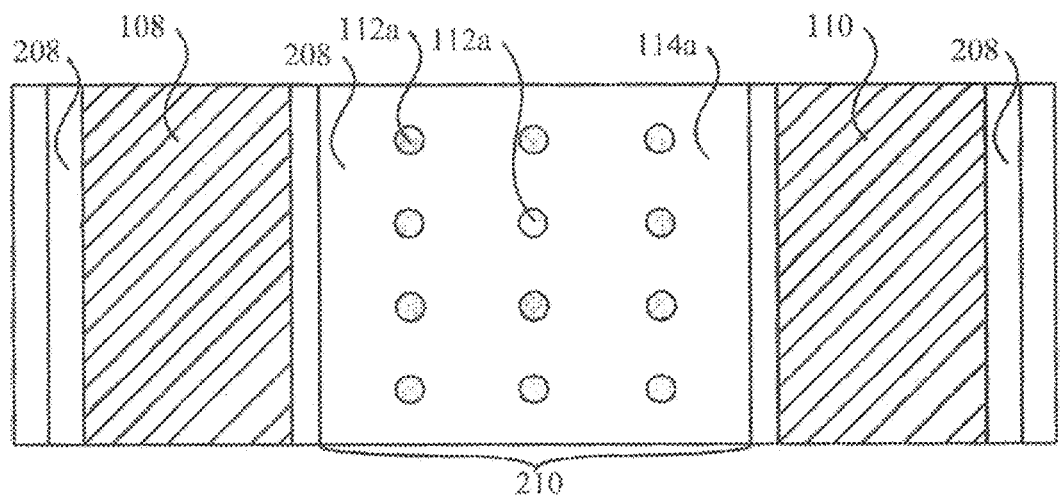
FIG. 2A is an exemplary illustrative top view of a diamond transistor pathogen virus detector, such as the pathogen virus detector of FIG. 1.
Figure 2B:
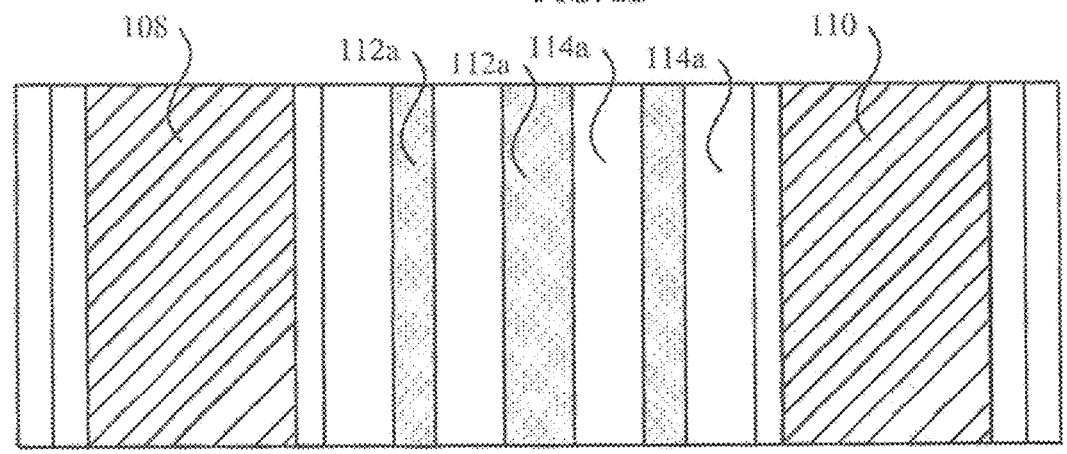
FIG. 2B is an exemplary illustrative top view of a diamond transistor pathogen virus detector, such as the pathogen virus detector of FIG. 1.

FIG. 2A shows a top-level view of a diamond transistor pathogen virus detector, such as the pathogen virus detector system 100 of FIG. 1. FIG. 2A includes a hydrophobic source area, such as source 108, a hydrophobic drain area, such as drain area 110, a plurality of hydrophillic GO conductive channels, such as GO conductive channel 112a, and a plurality of hydrophobic surface treatment areas 208, such as FGO gate oxide 114a portion.

By selectively providing hydrophobic and hydrophilic areas target molecules can be encouraged to cluster in the area of antibody mimic protein (AMP) structures to provide opportunities to bind the targets. The channel area, such as channel 112a, may be covered with GO material. The GO may provide a hydrophilic surface treatment which will tend to attract water and polar molecules. The source area, such as source 108, may be at least partially covered by FGO material. The FGO may provide a hydrophobic surface treatment which will tend to repel water and polar molecules.

The GO hydrophillic surface treatment areas, such as GO conductive channel 112a, may be formed by stacking a silicon layer, a silicon Dioxide layer, a diamond layer, and GO layer, and a linker layer. For example, GO conductive channel 112a may be formed from the silicon layer 102, the silicon dioxide layer 104, the undoped diamond layer 106, the first graphene oxide layer 112, and the linker layer 116.

Hydrophobic surface treatment areas, such as gate oxide 114a, may be formed by stacking a silicon layer, a silicon Dioxide layer, a diamond layer, a GO layer, an FGO layer, and a linker layer. For example, gate oxide 114a may be formed from the silicon layer 102, the silicon dioxide layer 104, the undoped diamond layer 106, the first graphene oxide layer 112, the second graphene oxide layer 114, and the linker layer 116.

FIG. 3 shows an exemplary block diagram of an embodiment of a method 300 for fabricating a diamond transistor pathogen virus detection, such as, but not limited to, the diamond transistor pathogen virus detector 100. Method 300 may include a step 302 of selecting a substrate; a step 304 of depositing fused silica; a step 306 of seeding the surface; a step 308 of depositing Nano-Crystalline Diamond (NCD); a step 310 of depositing contact metal; a step 312 of annealing the contact metal; a step 314 of spinning and baking a first graphene oxide (GO) layer; a step 316 of masking and etching the first GO layer; a step 318 of spinning and baking a second GO layer; a step 320 of plasma converting to the second GO layer to fluorinated graphene oxide (FGO) layer; a step 322 of masking and etching the FGO layer; a step 324 of depositing a linker layer; and a step 326 of pattern and etching the linker layer.

Step 302 of selecting a substrate may include selecting a 500 um thick silicon substrate. The result of step 302 may include a silicon layer, such as but not limited to, the silicon layer 102 of exemplary diamond transistor pathogen virus detector 100. Step 304 of depositing fused silica may include growing fused silica on the substrate of step 302. Step 304 may include using a diffusion process. The result of step 304 may include a silicon dioxide layer, such as but not limited to, the silicon dioxide layer 104 of detector 100.

Step 306 of seeding the surface may include seeding using a nanodiamond seed solution mixture and ultrasonicated in alcohol solution to promote nucleation and film agglomeration. Step 308 of depositing NCD may include exposing the seeded surface of step 306 to a methane, argon, and hydrogen plasma gas mixture in a chemical vapor deposition system to produce a thin nanocrystalline diamond film. Diamond growth may be realized using a hot filament or microwave chemical vapor deposition system (to a desired growth of 100 nm, for example). The result of step 308 may include an undoped diamond layer, such as but not limited to, the undoped diamond layer 106 of detector 100.

Step 310 of depositing contact metal may include depositing a layer of titanium/gold (TiAu) or another contact metal on the diamond film. Step 310 may result a source and a drain. for example, step 310 may create the source 108 and drain 110 of detector 100. Step 312 of annealing the contact metal may include metal anneal using rapid thermal annealing process.

Step 314 of spinning and baking the first graphene oxide GO layer may include depositing GO on top of a metal layer using a spin and bake process. For example, the graphene oxide layer may be added by spin coating using a solution of graphene oxide in an aqueous solution. After applying the solution to the substrate, a spin coater can be used to provide uniform coverage. The substrate may be heated to 100 deg C. for about 1 minute to set the graphene oxide layer. Step 316 of masking and etching the GO may include applying a mask to the graphene oxide and processing to mask off an active channel region. The result of steps 314 and 316 may be the GO conductive channel 112 of detector 100.

Step 318 of spinning and baking a second GO layer may include adding a second layer of GO that may be deposited using the spin and bake process. Step 320 of plasma converting to fluorinated graphene oxide (FGO) may include exposing to plasma conversion to convert the GO to FGO. For example, the device may be subjected to a fluorine environment in a PECVD tool using gas precursors $CHF_3$ and $CF_4$ at a ratio of 3:1 resulting in a layer of FGO less than 100 nm thick. The result of step 318 may be the second graphene oxide layer 114 of detector 100. Step 322 of masking and etching the FGO may include a mask and dry or wet chemistry etch of the FGO layer. For example, rinsing the device in a heated solution of water and ammonium fluoride to selectively strip Fluorine.

Step 324 of depositing a linker layer may include depositing an antigen linker layer. The result of step may be the applied to the FGO gate oxide 114a portion 114a of detector 100. For example, the exposed device area may be washed in Cysteamine for 30 minutes, followed by glutaraldehyde solution (5% in water) for another 30 min. The result of step 324 may include a linked layer, such as but not limited to, the linked layer 116 of detector 100.

Step 326 of pattern and etching the linker layer may include bonding antibody mimic proteins (AMP) to the linker layer, for example but not limited to, as binding AMP to linker layer 116. For example, target antigens such SARS-COV2 antibody, Ebola antibody, or the like, may be prepared in varying concentrations with Phosphate Buffer Saline (PBS) and allowed to conjugate with antigen linker layer during 30 min incubation of device at room temperature, followed by thorough washing with distilled water and dried with N2 gas. The FET structure that may result from method 300 may act as a bio FET to detect viruses, bacteria, or proteins specific to the bonded AMPs.

Figure 4:
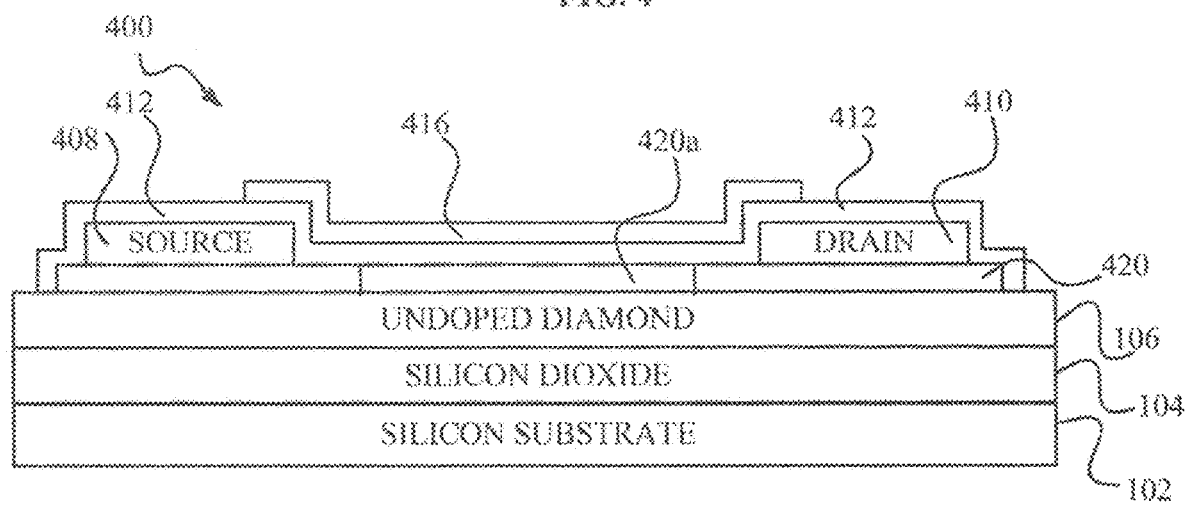
FIG. 4 is an exemplary illustrative side view of a nanowire diamond transistor pathogen virus detector.

FIG. 4 shows an exemplary nanowire diamond transistor pathogen virus detector 400, including a silicon substrate layer 102, a silicon dioxide layer 104, an undoped diamond layer 106, a doped diamond layer 420, the doped diamond layer including a nanowire portion 420a; a metal layer having a source 408 portion and a drain 410 portion, a graphene oxide (GO) layer 412, and a linked layer, such as linked layer 416.

Figure 5:
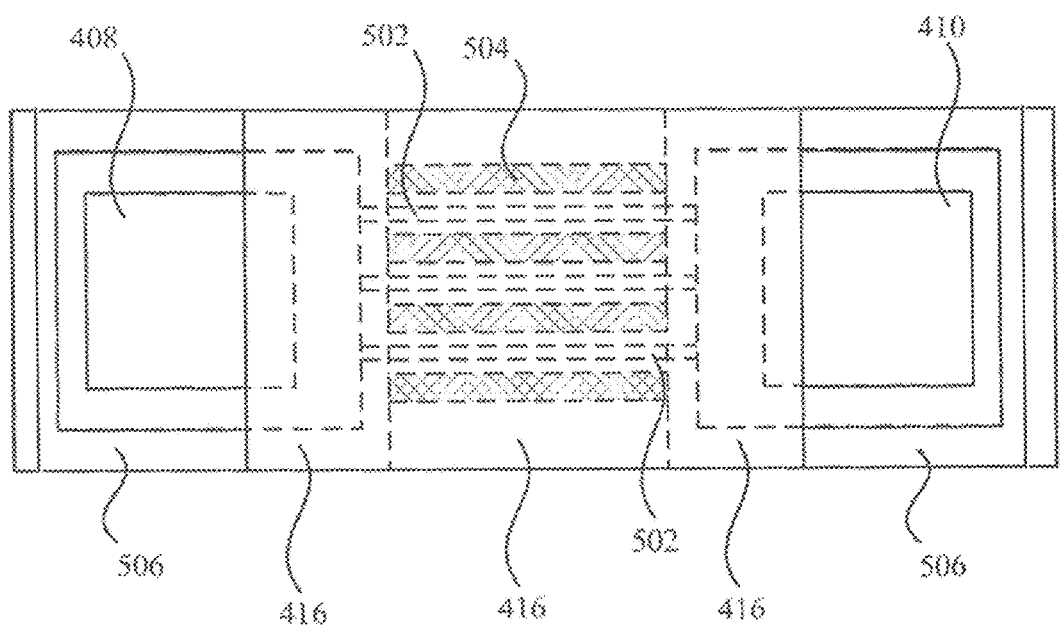
FIG. 5 is an exemplary illustrative top view of a diamond transistor pathogen virus detector, such as the nanowire diamond pathogen virus detector of FIG. 4.

FIG. 5 shows a top-level view of a nanowire diamond transistor pathogen virus detector, such as the pathogen virus detector 400 of FIG. 4. FIG. 5 includes a hydrophobic source area, such as source 408, a hydrophobic drain area, such as drain area 410, a plurality of hydrophobic FGO-coated nanowires 502 that may be formed in the nanowire portion 420a of the doped diamond layer 420, which may be under a linker layer, such as linker layer 416 that may cover a conductive channel between the source and drain; a plurality of GO portions 504 of a graphene oxide (GO) layer, such as GO layer 412, that are between the nanowire portions 420a. The GO portions 504 may provide a hydrophilic coating portion between the hydrophobic FGO-coated nanowires 502. FGO may provide a plurality of hydrophobic portions 506 of detector 400, such as near the source 408 and the drain 410.

Figure 6:
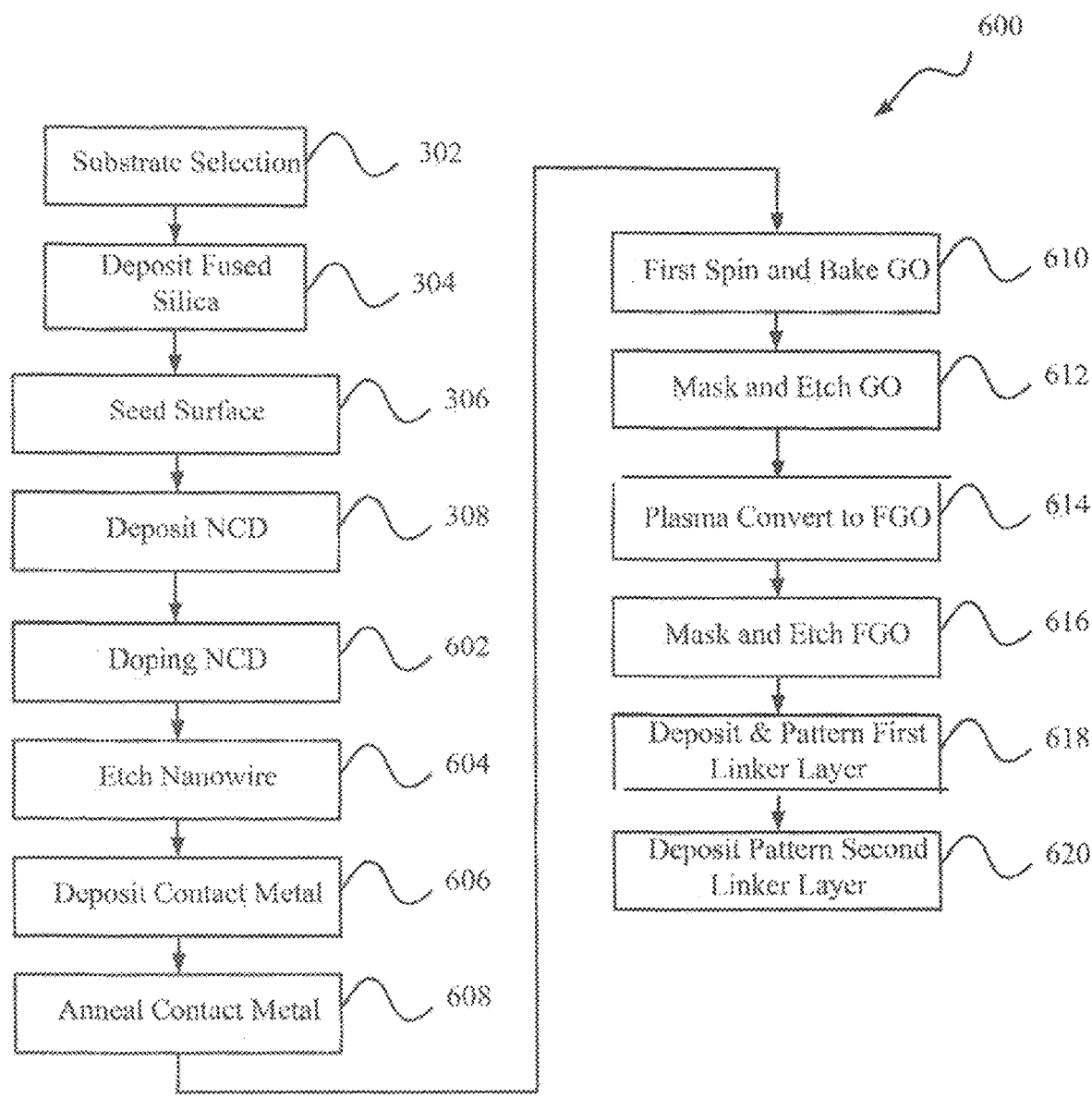
FIG. 6 is a second exemplary block diagram of an embodiment of a method for fabricating a diamond transistor pathogen virus detector, such as the nanowire diamond transistor pathogen virus detector of FIG. 4.

FIG. 6 shows a second exemplary block diagram of an embodiment of a method 600 for fabricating a nanowire diamond transistor pathogen virus detection. Method 600 may include a step 302 of selecting a substrate; a step 304 of depositing fused silica; a step 306 of seeding the surface; a step 308 of depositing NCD; a step 602 of doping the NCD; a step 604 of etching a nanowire; a step 606 of depositing contact metal; a step 608 of annealing the contact metal; a step 610 of spinning and baking a first graphene oxide (GO) layer; a step 612 of masking and etching the GO layer; a step 614 of plasma converting at least a portion of the GO layer to fluorinated graphene oxide (FGO); a step 616 of masking and etching the FGO layer; a step 618 of depositing a patterning a first linker layer; and a step 620 of depositing and patterning a second linker layer.

Step 602 of doping the NCD may include depositing and doping the nanowire and may include insitu n-type or p-type doping during NCD synthesis, or may include n-type or p-type ion implantation and annealing. Step 604 of etching a nanowire may include etching the diamond selectively to realize a nanowire by masking using aluminum and etching using reactive ion etching techniques. Step 606 of depositing contact metal may include depositing a layer of titanium/gold (TiAu) or another contact metal on the diamond film. For example, step 606 may result in a source and a drain. For example, step 606 may create the source 408 and drain 410 of detector 400. Step 608 of annealing the contact metal may include metal anneal using rapid thermal annealing. Step 610 of spinning and baking the first graphene oxide GO layer may include depositing GO on top of a metal layer using a spin and bake process. For example, the graphene oxide layer may be added by spin coating using a solution of graphene oxide in an aqueous solution. After applying the solution to the substrate, a spin coater can be used to provide uniform coverage. The substrate may be heated to 100 deg C. for about 1 minute to set the graphene oxide layer. Step 612 of masking and etching the GO may include applying a mask to the graphene oxide and processing to mask off an active channel region.

Step 614 of plasma converting to fluorinated graphene oxide (FGO) may include exposing to plasma conversion to convert the GO to FGO. Step 616 of masking and etching the FGO may include a mask and dry or wet chemistry etch of the FGO layer. For example, step 616 may include rinsing the device in a heated solution of water and ammonium fluoride to selectively strip Fluorine.

Step 618 of depositing a first linker layer may include depositing a first fibronectin linker layer that may be applied to a gate area. Step 620 may include depositing a second linker layer 620 that may include a second Antigen Mimetic Protein (AMP) linker layer. Step 620 may include bonding antibody mimic proteins (AMP) to the linker layer, The resulting FET structure will act as a bio FET to detect viruses, bacteria, or proteins specific to the bonded AMPs.

Figure 7:
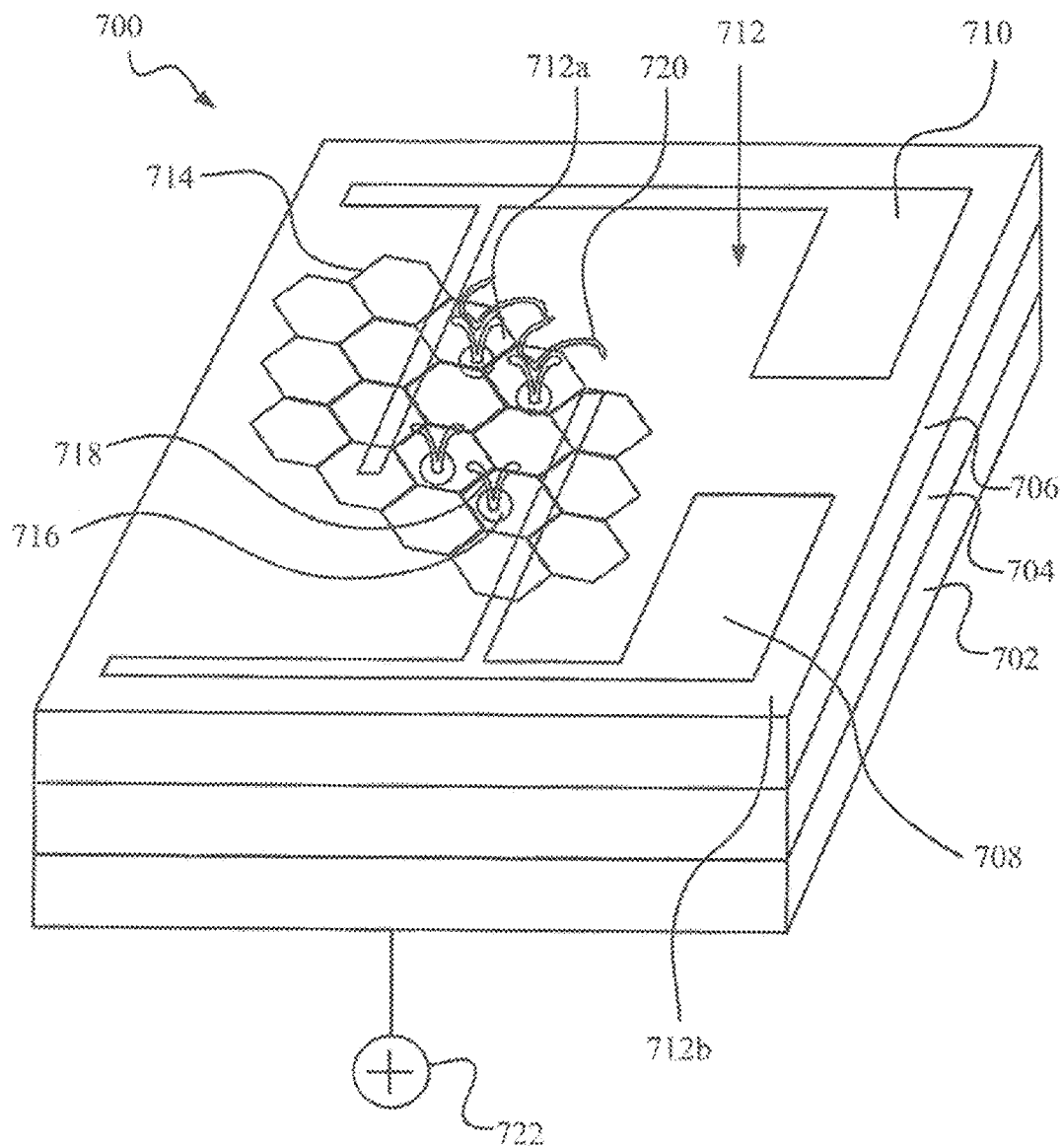
FIG. 7 is an exemplary illustrative perspective view of another diamond transistor pathogen virus detector.

FIG. 7 shows another exemplary diamond transistor pathogen virus detector 700 in contact with a pathogen 720, the detector 700 including a silicon layer 702, a silicon dioxide layer 704, an undoped diamond layer 706, a metal layer having a source 708 portion and a drain 710 portion, a top layer 712, that may include hydrophilic graphene oxide (GO) portions 712a and hydrophobic fluorinated graphene oxide (FGO) portions 712b, a graphene structure 714, a GO conductive channel 716, a plurality of pathogen receptors 718, and gate 722. When the pathogen receptors 718 bind to a pathogen 720, a change in operation of the detector 700 can be measured.

The multilayer diamond display system described, and method 200, may incorporate systems and methods previously disclosed and described in U.S. Patent Publication No. 2013/0026492, by Adam Khan, published on Jan. 31, 2013; U.S. Pat. No. 8,354,290, issued to Anirudha Sumant, et al, on Jan. 15, 2013; U.S. Pat. No. 8,933,462, issued to Adam Khan on Jan. 13, 2015; U.S. Patent Publication No. 2015/0206749, by Adam Khan, published on Jul. 23, 2015; and U.S. Patent Publication No. 2015/0295134, by Adam Khan, et al, published on Oct. 15, 2015, all of which are fully incorporated herein by reference.

The multilayer diamond display system described, and method 200, may incorporate systems and methods disclosed and described in: (a) Label-Free, Electrical Detection of the SARS Virus N-Protein with Nanowire Biosensors Utilizing Antibody Mimics as Capture Probes by Fumiaka N. Ishikawa et al. NIH Public Access; ACS Nano. Author Manuscript; available in PMC 2010 May 26; (b) Detection of Rota Virus with the Help of Nanomaterial Based Field Effect Transistor (BIO-FET) by Mudita Pant et al. Biosensor Journal 2017, 6:2; (c) Field-Effect Transistor Biosensor for Rapid Detection of Ebola Antigen by Yantao Chen et al. Scientific Reports 7:10974; (d) U.S. Patent Application 20110315962, titled Nanosensors, by Lieber et al., published Dec. 29, 2011; (e) U.S. Patent Application 20100078652, titled Diamond Electronic Devices Including A Surface And Methods For Their Manufacture, by Scarsbrook et al. published Apr. 1, 2010; (f) U.S. Patent Publication US20100087013, titled Nanosensors And Related Technologies, by Liber et al., published Apr. 8, 2010; (g) U.S. Patent Application 20080211040, titled Nanosensors, by Lieber et al., published Sep. 4, 2008; and (h) U.S. Patent Application 20070032052, titled Doped Elongated Semiconductors, Growing Such. Semiconductors, Devices Including Such Semiconductors, And Fabricating Such Devices, by Lieber et al., published Feb. 8, 2007.

This disclosure provides several preferred embodiments of fabrication, however, the performance characteristics and materials characteristics described in this application are not necessarily performance bounds or limitations of the invention. These disclosures merely demonstrate some aspects of the invention that have presently been tested.

The word "exemplary" is used herein to mean "serving as an example, instance, or illustration." Any embodiment or variant described herein as "exemplary" is not necessarily to be construed as preferred or advantageous over other embodiments or variants. All of the embodiments and variants described in this description are exemplary embodiments and variants provided to enable persons skilled in the art to make and use the invention, and not necessarily to limit the scope of legal protection afforded the appended claims.

The above description of the disclosed embodiments is provided to enable any person skilled in the art to make or use that which is defined by the appended claims. The following claims are not intended to be limited to the disclosed embodiments. Other embodiments and modifications will readily occur to those of ordinary skill in the art in view of these teachings. Therefore, the following claims are intended to cover all such embodiments and modifications when viewed in conjunction with the above specification and accompanying drawings.

The invention claimed is:

1. A transistor biomolecule detector, comprising:
   a nanocrystalline diamond layer,
   at least one of a graphene oxide layer and a fluorinated graphene oxide layer on the nanocrystalline diamond layer, arranged to define separate hydrophilic and hydrophobic areas; and
   a linker layer including a plurality of biomolecule receptors, wherein the transistor biomolecule detector functions as a biosensor field effect transistor.

* * * * *